US012349983B2

(12) United States Patent
Messerly et al.

(10) Patent No.: US 12,349,983 B2
(45) Date of Patent: Jul. 8, 2025

(54) SYSTEMS AND METHODS FOR ULTRASOUND-AND-BIOIMPEDANCE-BASED GUIDANCE OF MEDICAL DEVICES

(71) Applicant: Bard Access Systems, Inc., Salt Lake City, UT (US)

(72) Inventors: Shayne Messerly, Kaysville, UT (US); Anthony K. Misener, Bountiful, UT (US); Steffan Sowards, Salt Lake City, UT (US); Robin Scott Urry, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 574 days.

(21) Appl. No.: 17/687,476

(22) Filed: Mar. 4, 2022

(65) Prior Publication Data

US 2022/0280246 A1    Sep. 8, 2022

Related U.S. Application Data

(60) Provisional application No. 63/157,544, filed on Mar. 5, 2021.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/063* (2013.01); *A61B 5/068* (2013.01); *A61B 8/0841* (2013.01);
(Continued)

(58) Field of Classification Search
CPC ......... A61B 34/20; A61B 5/063; A61B 5/068; A61B 8/0841; A61B 8/4254;
(Continued)

(56) References Cited

U.S. PATENT DOCUMENTS

| 5,325,293 A | 6/1994 | Dorne |
| 5,549,554 A | 8/1996 | Miraki |

(Continued)

FOREIGN PATENT DOCUMENTS

| CN | 101854853 A | 10/2010 |
| CN | 105054962 A | 11/2015 |

(Continued)

OTHER PUBLICATIONS

Beigi, P. et al., "Enhancement of needle visualization and localization in ultrasound." International Journal of Computer Assisted Radiology and Surgery, vol. 16, No. 130, Sep. 2020 [Sep. 30, 2020] pp. 169-178.

(Continued)

*Primary Examiner* — Yi-Shan Yang
*Assistant Examiner* — Nicholas A Robinson
(74) *Attorney, Agent, or Firm* — Rutan & Tucker LLP

(57) ABSTRACT

Disclosed are systems and methods for ultrasound-and-bioimpedance-based guidance of medical devices. A system can include an ultrasound probe, a needle, a console, and a display screen. The ultrasound probe is configured to emit ultrasound pulses and receive reflected ultrasound pulses reflected back through one or more tissues for producing ultrasound images. The needle can be configured to emit, detect, or alternately emit and detect electrical currents passed through the one-or-more tissues disposed between a pair or more of system electrodes for measuring bioimpedance. The console can be configured to instantiate one or more console processes for the ultrasound-and-bioimpedance-based guidance with the ultrasound probe and the needle. The display screen is configured to display a graphical representation of the needle among anatomical features of the patient in the ultrasound images confirmed by the bioimpedance of the one-or-more tissues previously or (Continued)

instantly disposed between the pair-or-more of system electrodes.

22 Claims, 9 Drawing Sheets

(51) Int. Cl.
    *A61B 8/00*     (2006.01)
    *A61B 8/08*     (2006.01)

(52) U.S. Cl.
    CPC .......... *A61B 8/4254* (2013.01); *A61B 8/4488* (2013.01); *A61B 8/463* (2013.01); *A61B 2034/2053* (2016.02); *A61B 2034/2063* (2016.02)

(58) Field of Classification Search
    CPC .................. A61B 8/4488; A61B 8/463; A61B 2034/2053; A61B 2034/2063; A61B 8/461; A61B 5/0538; A61B 8/5261; A61B 8/5292; A61B 2034/2065; A61B 2034/2072

See application file for complete search history.

(56) References Cited

U.S. PATENT DOCUMENTS

| | | |
|---|---|---|
| 5,573,529 A | 11/1996 | Haak et al. |
| 5,908,387 A | 6/1999 | LeFree et al. |
| 5,970,119 A | 10/1999 | Hofmann |
| 5,997,497 A | 12/1999 | Nita et al. |
| 6,012,034 A | 1/2000 | Hamparian et al. |
| 6,074,367 A | 6/2000 | Hubbell |
| 6,543,642 B1 | 4/2003 | Milliorn |
| 6,554,771 B1 | 4/2003 | Buil et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,687,386 B1 | 2/2004 | Ito et al. |
| 6,702,749 B2 | 3/2004 | Paladini et al. |
| 6,754,608 B2 | 6/2004 | Svanerudh et al. |
| 6,840,379 B2 | 1/2005 | Franks-Farah et al. |
| 6,857,196 B2 | 2/2005 | Dalrymple |
| 7,831,449 B2 | 11/2010 | Ying et al. |
| 9,521,961 B2 | 12/2016 | Silverstein et al. |
| 9,756,766 B2 | 9/2017 | Best |
| 9,949,720 B2 | 4/2018 | Southard et al. |
| 9,950,139 B2 | 4/2018 | Blanchard et al. |
| 10,849,689 B1 | 12/2020 | Hu et al. |
| 11,462,324 B1 | 10/2022 | Roh et al. |
| 11,844,656 B2 | 12/2023 | Urabe et al. |
| 11,896,425 B2 | 2/2024 | Dhatt et al. |
| 11,974,813 B1 | 5/2024 | Donhowe et al. |
| 2003/0047126 A1 | 3/2003 | Tomaschko |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0165299 A1 | 7/2005 | Kressy et al. |
| 2006/0004290 A1 | 1/2006 | Smith et al. |
| 2006/0015039 A1 | 1/2006 | Cassidy et al. |
| 2006/0020256 A1 | 1/2006 | Bell et al. |
| 2007/0043341 A1 | 2/2007 | Anderson et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2007/0260213 A1 | 11/2007 | Williams et al. |
| 2008/0009747 A1* | 1/2008 | Saadat .................... A61B 1/04 604/510 |
| 2008/0033293 A1 | 2/2008 | Beasley et al. |
| 2008/0033759 A1 | 2/2008 | Finlay |
| 2008/0051657 A1 | 2/2008 | Rold |
| 2008/0058963 A1 | 3/2008 | Garibaldi et al. |
| 2008/0161687 A1 | 7/2008 | Suri et al. |
| 2008/0177186 A1 | 7/2008 | Slater et al. |
| 2008/0300491 A1 | 12/2008 | Bonde et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0182224 A1 | 7/2009 | Shmarak et al. |
| 2009/0234328 A1 | 9/2009 | Cox et al. |
| 2009/0306509 A1 | 12/2009 | Pedersen et al. |
| 2010/0080427 A1 | 4/2010 | Yeluri et al. |
| 2010/0211026 A2 | 8/2010 | Sheetz et al. |
| 2010/0305442 A1 | 12/2010 | Tierney et al. |
| 2010/0312121 A1 | 12/2010 | Guan |
| 2011/0002884 A1 | 1/2011 | McCauley et al. |
| 2011/0071404 A1 | 3/2011 | Schmitt et al. |
| 2011/0166451 A1 | 7/2011 | Blaivas et al. |
| 2011/0295108 A1 | 12/2011 | Cox et al. |
| 2011/0313293 A1 | 12/2011 | Lindekugel et al. |
| 2012/0078103 A1 | 3/2012 | Tashiro et al. |
| 2012/0143029 A1 | 6/2012 | Silverstein et al. |
| 2012/0165679 A1 | 6/2012 | Orome et al. |
| 2012/0197132 A1 | 8/2012 | O'Connor |
| 2012/0253200 A1 | 10/2012 | Stolka et al. |
| 2013/0006102 A1 | 1/2013 | Wilkes et al. |
| 2013/0102889 A1 | 4/2013 | Southard et al. |
| 2013/0131499 A1 | 5/2013 | Chan et al. |
| 2013/0218024 A1 | 8/2013 | Boctor et al. |
| 2013/0261553 A1 | 10/2013 | Sheldon et al. |
| 2014/0155744 A1 | 6/2014 | Pameijer |
| 2014/0275997 A1 | 9/2014 | Chopra et al. |
| 2014/0287393 A1 | 9/2014 | Kumar et al. |
| 2014/0343406 A1* | 11/2014 | Damjanovic ...... A61N 1/36017 600/424 |
| 2015/0148668 A1 | 5/2015 | Stolka et al. |
| 2015/0182144 A1 | 7/2015 | Bharat et al. |
| 2015/0216442 A1 | 8/2015 | Lavy et al. |
| 2015/0250437 A1 | 9/2015 | Zaiki |
| 2015/0272553 A1 | 10/2015 | Thattari Kandiyil et al. |
| 2015/0320325 A1 | 11/2015 | Sheehan et al. |
| 2015/0320481 A1* | 11/2015 | Cosman, Jr. ............ A61B 34/10 606/35 |
| 2015/0359991 A1* | 12/2015 | Dunbar ................ A61B 8/4254 600/424 |
| 2016/0128719 A1 | 5/2016 | Cermak |
| 2016/0174937 A1 | 6/2016 | Bakshi et al. |
| 2016/0213398 A1 | 7/2016 | Liu |
| 2016/0300120 A1 | 10/2016 | Haas et al. |
| 2016/0302772 A1 | 10/2016 | Cummins et al. |
| 2016/0374644 A1 | 12/2016 | Mauldin, Jr. et al. |
| 2017/0035514 A1 | 2/2017 | Fox et al. |
| 2017/0056062 A1 | 3/2017 | Buljubasic |
| 2017/0079551 A1 | 3/2017 | Henkel et al. |
| 2017/0188990 A1 | 7/2017 | Von Allmen et al. |
| 2017/0245831 A1* | 8/2017 | Nishigaki ................ A61B 8/52 |
| 2017/0265946 A1 | 9/2017 | Ramachandran et al. |
| 2017/0290563 A1 | 10/2017 | Cole et al. |
| 2018/0015256 A1 | 1/2018 | Southard et al. |
| 2018/0036084 A1 | 2/2018 | Krimsky |
| 2018/0061546 A1 | 3/2018 | Ma et al. |
| 2018/0125450 A1 | 5/2018 | Blackbourne et al. |
| 2018/0132944 A1 | 5/2018 | Yan et al. |
| 2018/0228465 A1 | 8/2018 | Southard et al. |
| 2018/0289929 A1 | 10/2018 | Ma et al. |
| 2018/0310955 A1 | 11/2018 | Lindekugel et al. |
| 2019/0000478 A1* | 1/2019 | Messerly ............ A61B 18/1445 |
| 2019/0026438 A1 | 1/2019 | Ma et al. |
| 2019/0298278 A1 | 10/2019 | Nachabe et al. |
| 2019/0374290 A1 | 12/2019 | Stolka et al. |
| 2020/0090331 A1 | 3/2020 | Mansi et al. |
| 2020/0113540 A1 | 4/2020 | Gijsbers et al. |
| 2020/0230391 A1 | 7/2020 | Burkholz et al. |
| 2020/0234812 A1 | 7/2020 | Willybiro et al. |
| 2020/0237403 A1 | 7/2020 | Southard et al. |
| 2020/0245969 A1 | 8/2020 | Tung et al. |
| 2020/0297235 A1* | 9/2020 | Sanchez ................ A61B 5/262 |
| 2020/0315592 A1 | 10/2020 | Soleimani et al. |
| 2020/0359990 A1 | 11/2020 | Poland et al. |
| 2021/0015448 A1 | 1/2021 | Sokulin et al. |

(56) References Cited

U.S. PATENT DOCUMENTS

| | | |
|---|---|---|
| 2021/0045717 A1 | 2/2021 | Schwab |
| 2021/0059636 A1 | 3/2021 | Durfee et al. |
| 2021/0085282 A1 | 3/2021 | Prince |
| 2021/0138130 A1 | 5/2021 | Kotanko et al. |
| 2021/0169585 A1 | 6/2021 | Prince et al. |
| 2021/0186456 A1 | 6/2021 | Prince |
| 2021/0201080 A1 | 7/2021 | Kitahara |
| 2021/0275256 A1 | 9/2021 | Sowards et al. |
| 2021/0315542 A1 | 10/2021 | Oura et al. |
| 2022/0022969 A1 | 1/2022 | Misener |
| 2022/0027257 A1 | 1/2022 | Harutyunyan et al. |
| 2022/0039685 A1 | 2/2022 | Misener et al. |
| 2022/0054869 A1 | 2/2022 | Stein et al. |
| 2022/0096797 A1 | 3/2022 | Prince |
| 2022/0101980 A1 | 3/2022 | Rothenberg et al. |
| 2022/0104886 A1 | 4/2022 | Blanchard et al. |
| 2022/0117582 A1 | 4/2022 | McLaughlin et al. |
| 2022/0142608 A1 | 5/2022 | Matsumoto |
| 2022/0160434 A1 | 5/2022 | Messerly et al. |
| 2022/0189610 A1 | 6/2022 | Long et al. |
| 2022/0230714 A1 | 7/2022 | Batman et al. |
| 2022/0241014 A1 | 8/2022 | Kleyman et al. |
| 2022/0304652 A1 | 9/2022 | Peterson et al. |
| 2022/0392642 A1 | 12/2022 | Dasi et al. |
| 2022/0401157 A1 | 12/2022 | Sowards et al. |
| 2022/0406460 A1 | 12/2022 | Golan et al. |
| 2023/0030941 A1 | 2/2023 | Han |
| 2023/0121370 A1 | 4/2023 | Sowards et al. |
| 2023/0147164 A1 | 5/2023 | Sowards et al. |
| 2023/0148993 A1 | 5/2023 | Sowards et al. |
| 2023/0225702 A1 | 7/2023 | Sakalauskas |
| 2023/0260107 A1 | 8/2023 | Dhatt et al. |
| 2023/0329748 A1 | 10/2023 | Sowards et al. |
| 2023/0338003 A1 | 10/2023 | Misener et al. |
| 2023/0380906 A1 | 11/2023 | Misener et al. |
| 2023/0404683 A1 | 12/2023 | Schmidt et al. |
| 2023/0420105 A1 | 12/2023 | Misener et al. |
| 2024/0008894 A1 | 1/2024 | Sowards et al. |
| 2024/0245386 A1 | 7/2024 | Prince |
| 2024/0274297 A1 | 8/2024 | Sillesen et al. |
| 2025/0000585 A1 | 1/2025 | Sinha et al. |

FOREIGN PATENT DOCUMENTS

| | | |
|---|---|---|
| CN | 216167530 U | 4/2022 |
| EP | 0788329 A1 * | 8/1997 |
| EP | 1504713 A1 | 2/2005 |
| EP | 0788329 B1 | 12/2006 |
| JP | 2018175547 A | 11/2018 |
| KR | 20180070878 A | 6/2018 |
| NO | 2021113733 A1 | 6/2021 |
| WO | 2013059714 A1 | 4/2013 |
| WO | 2014053934 A1 | 4/2014 |
| WO | 2015/017270 A1 | 2/2015 |
| WO | 2018/026878 A1 | 2/2018 |
| WO | 2019/232451 A1 | 12/2019 |
| WO | 2020/002620 A1 | 1/2020 |
| WO | 2020150501 A1 | 7/2020 |
| WO | 2020160550 A1 | 8/2020 |
| WO | 2020/186198 A1 | 9/2020 |
| WO | 2022/067101 A1 | 3/2022 |
| WO | 2022/072727 A2 | 4/2022 |
| WO | 2022/081904 A1 | 4/2022 |
| WO | 2022/150411 A1 | 7/2022 |
| WO | 2022/187701 A1 | 9/2022 |
| WO | 2022212414 A1 | 10/2022 |
| WO | 2022/271728 A1 | 12/2022 |
| WO | 2023064492 A1 | 4/2023 |
| WO | 2023081414 A1 | 5/2023 |
| WO | 2023091427 A1 | 5/2023 |
| WO | 2023205019 A1 | 10/2023 |
| WO | 2023205052 A1 | 10/2023 |
| WO | 2023230284 A1 | 11/2023 |
| WO | 2023244640 A1 | 12/2023 |
| WO | 2023250001 A1 | 12/2023 |
| WO | 2024010874 A1 | 1/2024 |

OTHER PUBLICATIONS

PCT/US2023/018340 filed Apr. 12, 2023 International Seach Report and Written Opinion dated Jul. 20, 2023.

PCT/US2023/018680 filed Apr. 14, 2023 International Seach Report and Written Opinion dated Aug. 11, 2013.

PCT/US2023/023616 filed May 25, 2023 International Search Report and Written Opinion dated Aug. 16, 2023.

U.S. Appl. No. 17/725,370, filed Apr. 20, 2022 Non-Final Office Action dated Aug. 4, 2023.

PCT/US2012/061182 International Seach Report and Written Opinion dated Mar. 11, 2013.

PCT/US2020/063441 filed Dec. 4, 2020 International Search Report and Written Opinion dated Mar. 19, 2021.

PCT/US2021/052055 filed Sep. 24, 2021 International Search Report and Written Opinion dated Dec. 20, 2021.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

U.S. Appl. No. 13/656,563, filed Oct. 19, 2012 Decision on Appeal dated Nov. 1, 2017.

U.S. Appl. No. 13/656,563, filed Oct. 19, 2012 Examiner's Answer dated Nov. 16, 2015.

U.S. Appl. No. 13/656,563, filed Oct. 19, 2012 Final Office Action dated Dec. 5, 2014.

U.S. Appl. No. 13/656,563, filed Oct. 19, 2012 Non-Final Office Action dated Jul. 18, 2014.

U.S. Appl. No. 15/951,903, filed Apr. 12, 2018 Advisory Action dated Dec. 22, 2020.

U.S. Appl. No. 15/951,903, filed Apr. 12, 2018 Board Decision dated Apr. 20, 2022.

U.S. Appl. No. 15/951,903, filed Apr. 12, 2018 Examiner's Answer dated Jun. 3, 2021.

U.S. Appl. No. 15/951,903, filed Apr. 12, 2018 Final Office Action dated Oct. 13, 2020.

U.S. Appl. No. 15/951,903, filed Apr. 12, 2018 Non-Final Office Action dated May 22, 2020.

U.S. Appl. No. 15/951,903, filed Apr. 12, 2018 Notice of Allowance dated May 2, 2022.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

PCT/US2022/034380 filed Jun. 21, 2022 International Search Report and Written Opinion dated Oct. 5, 2022.

PCT/US2022/046606 filed Oct. 13, 2022 International Search Report and Written Opinion dated Feb. 6, 2023.

PCT/US2022/049042 filed Nov. 4, 2022 International Search Report and Written Opinion dated Mar. 1, 2023.

PCT/US2022/049989 filed Nov. 15, 2022 International Search Report and Written Opinion dated Feb. 6, 2023.

U.S. Appl. No. 17/112,735, filed Dec. 4, 2022 Non-Final Office Action dated Oct. 26, 2022.

U.S. Appl. No. 17/112,725, filed Dec. 4, 2020 Final Office Action dated Apr. 14, 2023.

U.S. Appl. No. 17/485,035, filed Sep. 24, 2021 Non-Final Office Action dated May 3, 2023.

U.S. Appl. No. 17/725,370, filed Apr. 20, 2022 Restriction Requirement dated Apr. 27, 2023.

U.S. Appl. No. 17/707,662, filed Mar. 29, 2022 Advisory Action dated Feb. 23, 2024.

U.S. Appl. No. 17/707,662, filed Mar. 29, 2022 Final Office Action dated Apr. 22, 2024.

U.S. Appl. No. 17/707,662, filed Mar. 29, 2022 Final Office Action dated Dec. 20, 2023.

(56) References Cited

OTHER PUBLICATIONS

U.S. Appl. No. 17/724,371, filed Apr. 19, 2022 Non-Final Office Action dated Apr. 12, 2024.
U.S. Appl. No. 17/725,370, filed Apr. 20, 2022 Final Office Action dated Feb. 15, 2024.
U.S. Appl. No. 17/825,976, filed May 26, 2022 Restriction Requirement dated Apr. 12, 2024.
U.S. Appl. No. 17/859,980, filed Jul. 7, 2022 Non-Final Office Action dated Jul. 1, 2024.
PCT/US2023/025259 filed Jun. 14, 2023 International Search Report and Written Opinion dated Sep. 25, 2023.
PCT/US2023/025845 filed Jun. 21, 2023 International Search Report and Written Opinion dated Sep. 26, 2023.
PCT/US2023/027042 filed Jul. 6, 2023 International Search Report and Written Opinion dated Oct. 10, 2023.
Schmidt G A et al Ultrasound-guided 1-22 vascular access in critical illness Intensive Care Medicine Springer Berlin Heidelberg Berlin/Heidelberg vol. 45 No. 4 Feb. 18, 2019 Feb. 18, 2019 pp. 434-446 XP036747615 ISSN 0342-4642 DOI 10.1007/S00134-019-05564-7 retrieved on 2019-02-181.
U.S. Appl. No. 17/485,035, filed Sep. 24, 2021 Notice of Allowance dated Nov. 8, 2023.
U.S. Appl. No. 17/707,662, filed Mar. 29, 2022 Non-Final Office Action dated Oct. 17, 2023.
Murphy, Ethan K., et al., "Phantom Studies of Fused-Data TREIT Using Only Biopsy-Probe Electrodes" IEEE Transactions On Medical Imaging, IEEE, USA. vol. 39 No. 114, May 2020. (May 4, 2020).
PCT/US2020/063441 filed Dec. 4, 2020 International Preliminary Report on Patentability dated May 17, 2022.
PCT/US2022/019017 filed Mar. 4, 2022 International Search Report and Written Opinion dated Jun. 14, 2022.
PCT/US2022/022400 filed Mar. 29, 2022 International Search Report and Written Opinion dated Jul. 8, 2022.
U.S. Appl. No. 17/724,371, filed Apr. 19, 2022 Advisory Action dated Sep. 20, 2024.
U.S. Appl. No. 17/724,371, filed Apr. 19, 2022 Final Office Action dated Jul. 24, 2024.
U.S. Appl. No. 17/725,370, filed Apr. 20, 2022 Notice of Allowance dated Sep. 18, 2024.
U.S. Appl. No. 17/825,976, filed May 26, 2022 Non-Final Office Action dated Oct. 4, 2024.
U.S. Appl. No. 17/849,455, filed Jun. 24, 2022 Non-Final Office Action dated Jul. 18, 2024.
U.S. Appl. No. 17/981,313, filed Nov. 4, 2022 Non-Final Office Action dated Oct. 8, 2024.
U.S. Appl. No. 18/601,980, filed Mar. 11, 2024 Non-Final Office Action dated Sep. 27, 2024.
PCT/US2023/025845 filed Jun. 21, 2023 International Preliminary Report on Patentability dated Dec. 18, 2024.
U.S. Appl. No. 17/707,662, filed Mar. 29, 2022 Examiner's Answer dated Oct. 23, 2024.
U.S. Appl. No. 17/724,371, filed Apr. 19, 2022 Non-Final Office Action dated Nov. 26, 2024.
U.S. Appl. No. 17/849,455, filed Jun. 24, 2022 Advisory Action dated Dec. 17, 2024.
U.S. Appl. No. 17/849,455, filed Jun. 24, 2022 Final Office Action dated Nov. 7, 2024.
U.S. Appl. No. 17/849,455, filed Jun. 24, 2022 Non-Final Office Action dated Jan. 24, 2025.
U.S. Appl. No. 17/859,980, filed Jul. 7, 2022 Final Office Action dated Dec. 5, 2024.
U.S. Appl. No. 17/965,657, filed Oct. 13, 2022 Non-Final Office Action dated Jan. 6, 2025.
U.S. Appl. No. 18/601,980, filed Mar. 11, 2024 Notice of Allowance dated Jan. 10, 2025.
U.S. Appl. No. 17/724,371, filed Apr. 19, 2022 Final Office Action dated Mar. 7, 2025.
U.S. Appl. No. 17/825,976, filed May 26, 2022 Final Office Action dated Mar. 25, 2025.
U.S. Appl. No. 17/841,541, filed Jun. 15, 2022 Non-Final Office Action dated Mar. 14, 2025.
U.S. Appl. No. 17/845,818, filed Jun. 21, 2022 Restriction Requirement dated Feb. 10, 2025.
U.S. Appl. No. 17/859,980, filed Jul. 7, 2022 Advisory Action dated Feb. 10, 2025.
U.S. Appl. No. 17/987,717, filed Nov. 15, 2022 Non-Final Office Action dated Mar. 21, 2025.

* cited by examiner

SYSTEMS AND METHODS FOR ULTRASOUND-AND-BIOIMPEDANCE-BASED GUIDANCE OF MEDICAL DEVICES

PRIORITY

This application claims the benefit of priority to U.S. Provisional Application No. 63/157,544, filed Mar. 5, 2021, which is incorporated by reference in its entirety into this application.

BACKGROUND

Ultrasound-based guidance of medical devices is routine in a variety of medical procedures for diagnosing and treating diseases. For example, ultrasound-based guidance can be used to guide a biopsy needle to a suspected tumor within a patient for a needle biopsy. Such ultrasound-based guidance can include identifying a target (e.g., the suspected tumor) within the patient using an ultrasound probe, estimating a needle trajectory in the patient from an insertion point, inserting the needle into the patient at the chosen insertion point, adjusting the ultrasound probe if needed for better visualization of the needle, and following the needle trajectory to the target with the needle while making any necessary adjustments to the needle trajectory in accordance with the visualization of the needle. Notwithstanding clear successes in the ultrasound-based guidance of medical devices for diagnosing and treating diseases, challenges to better diagnoses and treatments remain such as being able to differentiate between different tissues in ultrasound imagery.

Disclosed herein are systems and methods for ultrasound-and-bioimpedance-based guidance of medical devices that address the foregoing.

SUMMARY

Disclosed herein is an ultrasound system with, in some embodiments, ultrasound-and-bioimpedance-based guidance for accessing a target within a patient. In such embodiments, the system includes an ultrasound probe, a needle, a console, and a display screen. The ultrasound probe includes an array of ultrasound transducers. The array of ultrasound transducers is configured to emit ultrasound pulses into the patient and receive reflected ultrasound pulses reflected back through one or more tissues for producing ultrasound images. The needle includes a needle hub and one or more needle electrodes in a distal portion of a needle shaft proximate a needle tip. The one-or-more needle electrodes are configured to emit, detect, or alternately emit and detect electrical currents passed through the one-or-more tissues disposed between a pair or more of system electrodes for measuring bioimpedance. The console includes one or more processors, primary memory including read-only memory ("ROM") and random-access memory ("RAM"), and instructions stored in the ROM. The instructions are configured to instantiate one or more console processes in the RAM for the ultrasound-and-bioimpedance-based guidance with the ultrasound probe and the needle when operably connected to the console. The display screen is operably connected to the console for the ultrasound-and-bioimpedance-based guidance. The display screen is configured to display a graphical representation of the needle among anatomical features of the patient in the ultrasound images confirmed by the bioimpedance of the one-or-more tissues previously or instantly disposed between the pair-or-more of system electrodes.

In some embodiments, the one-or-more needle electrodes include a single needle electrode.

In some embodiments, the ultrasound system further includes a needle guide. The needle guide is configured for coupling with a needle-guide attachment point of the ultrasound probe. The needle guide, the needle-guide attachment point, and the ultrasound probe include electronic circuitry configured to operably connect the needle to the console when a) the needle guide is coupled with the needle-guide attachment point and b) the needle is inserted into the needle guide and makes electrical contact with a ring electrical contact of the needle guide.

In some embodiments, the needle guide includes conductive inward-facing protrusions. The protrusions are configured to establish an electrical connection with outward-facing receptacles of the needle-guide attachment point when the needle guide is coupled with the needle-guide attachment point.

In some embodiments, the protrusions include barrier-piercing points. The barrier-piercing points are configured to a) pierce a protective film-based barrier when used over the ultrasound probe and b) establish the electrical connection with the receptacles of the needle-guide attachment point. The receptacles are shaped to accommodate the barrier-piercing points of the protrusions.

In some embodiments, the ultrasound system further includes a needle connector and a needle cable between the needle hub and the needle connector. The needle connector and the needle cable are configured to operably connect the needle to the console.

In some embodiments, the ultrasound system further includes an electrode assembly. The electrode assembly includes an external electrode, an electrode-assembly connector, and an electrode-assembly cable between the external electrode and the electrode-assembly electrode connector. The external electrode is configured to be adhered to skin of the patient. The electrode-assembly connector is configured to be connected to the console. The electrode-assembly cable is configured to operably connect the external electrode to the console through the electrode-assembly connector. The single needle electrode and the external electrode is the pair-or-more of system electrodes for measuring bioimpedance.

In some embodiments, the one-or-more needle electrodes include a pair of needle electrodes. The pair of needle electrodes are the pair-or-more of system electrodes for measuring bioimpedance.

In some embodiments, the one-or-more needle electrodes include two pairs of needle electrodes. The two pairs of needle electrodes are the pair-or-more of system electrodes for measuring bioimpedance.

In some embodiments, the needle further includes a needle connector. The needle connector is configured as a needle guide for coupling with a needle-guide attachment point of the ultrasound probe. The needle connector, a needle cable between the needle hub and the needle connector, the needle-guide attachment point, and the ultrasound probe include electronic circuitry configured to operably connect the needle to the console when the needle connector is coupled with the needle-guide attachment point.

In some embodiments, the needle further includes a needle connector and a needle cable between the needle hub and the needle connector. The needle connector and the needle cable are configured to operably connect the needle to the console.

In some embodiments, the one-or-more console processes include an ultrasound image-producing console process, a bioimpedance-measuring console process, and a correlating console process. The ultrasound image-producing console process is configured for producing the ultrasound images of the anatomical features from the reflected ultrasound pulses. The bioimpedance-measuring console process is configured for measuring the bioimpedance from the electrical currents passed through the one-or-more tissues disposed between the pair-or-more of system electrodes. The correlating console process is configured for correlating the bioimpedance of the one-or-more tissues with the anatomical features in the ultrasound images. The correlating console process is in accordance with correlating logic and at least the bioimpedance of the one-or-more tissues.

In some embodiments, the one-or-more console processes include a colorizing console process. The colorizing console process is configured for colorizing the one-or-more tissues of the ultrasound images on the display screen. The colorizing console process is in accordance with colorizing logic and at least the bioimpedance of the one-or-more tissues.

In some embodiments, the one-or-more console processes include a tissue transition-alerting console process. The tissue transition-alerting console process is configured for issuing a tissue-transition alert when the needle transitions from a tissue to another tissue of the one-or-more tissues. The tissue transition-alerting console process is in accordance with tissue-transition logic and at least the bioimpedance of the one-or-more tissues.

In some embodiments, the one-or-more console processes include an access-confirming console process. The access-confirming console process is configured for confirming access to the target. The access-confirming console process is in accordance with access-confirmation logic and at least the bioimpedance of the one-or-more tissues.

In some embodiments, the one-or-more console processes include a warning-issuing console process. The warning-issuing console process is configured for issuing a warning when access to the target is at risk of being lost. The warning-issuing console process is in accordance with warning logic and at least the bioimpedance of the one-or-more tissues.

In some embodiments, the one-or-more console processes include a trajectory-drawing console process. The trajectory-drawing console process is configured for drawing a trajectory on the display screen from the graphical representation of the needle to the target. The trajectory-drawing console process is in accordance with trajectory logic and readings provided by an array of magnetic sensors on the ultrasound probe for determining the position and orientation of the needle.

Also disclosed herein is a method of an ultrasound system for accessing a target within a patient with, in some embodiments, ultrasound-and-bioimpedance-based guidance. In such embodiments, the method includes an instantiating step, a plurality of ultrasound image-producing steps, a bioimpedance-measuring step, and a displaying step. The instantiating step includes instantiating one or more console processes in RAM of a console from instructions stored in ROM of the console. One or more processors of the console are configured to process at least reflected ultrasound pulses and detected electrical currents for the ultrasound-and-bioimpedance-based guidance. The plurality of ultrasound image-producing steps include producing ultrasound images of anatomical features of the patient in accordance with an ultrasound image-producing console process. The ultrasound image-producing console process is configured for processing the reflected ultrasound pulses resulting from ultrasound pulses emitted into the patient by an ultrasound probe and subsequently reflected back through one or more tissues of the patient. The bioimpedance-measuring step includes measuring bioimpedance of the one-or-more tissues in accordance with a bioimpedance-measuring console process. The bioimpedance-measuring console process is configured for processing the detected electrical currents passed through the one-or-more tissues when disposed between a pair or more of system electrodes including one or more needle electrodes of a needle. The displaying step includes displaying on a display screen a graphical representation of the needle among the anatomical features in the ultrasound images. The anatomical features are confirmed by the bioimpedance of the one-or-more tissues previously or instantly disposed between the pair-or-more of system electrodes.

In some embodiments, the method further includes a correlating step. The correlating step includes correlating the bioimpedance of the one-or-more tissues with the anatomical features in the ultrasound images. The correlating step is performed in accordance with a correlating console process using correlating logic and at least the bioimpedance of the one-or-more tissues.

In some embodiments, the method further includes a colorizing step. The colorizing step includes colorizing the one-or-more tissues of the ultrasound images on the display screen. The colorizing step is performed in accordance with a colorizing console process using colorizing logic and at least the bioimpedance of the one-or-more tissues.

In some embodiments, the method further includes an alert-issuing step. The alert-issuing step includes issuing a tissue-transition alert when the needle transitions from a tissue to another tissue of the one-or-more tissues. The tissue-transition alert is performed in accordance with a tissue transition-alerting console process using tissue-transition logic and at least the bioimpedance of the one-or-more tissues.

In some embodiments, the method further includes an access-confirming step. The access-confirming step includes confirming access to the target. The access-confirming step is performed in accordance with an access-confirming console process using access-confirmation logic and at least the bioimpedance of the one-or-more tissues.

In some embodiments, the method further includes a warning-issuing step. The warning-issuing step includes issuing a warning when access to the target is at risk of being lost. The warning-issuing step is performed in accordance with a warning-issuing console process using warning logic and at least the bioimpedance of the one-or-more tissues.

In some embodiments, the method further includes a trajectory-drawing step. The trajectory-drawing step includes drawing a trajectory on the display screen from the graphical representation of the needle to the target. The trajectory-drawing step is performed in accordance with a trajectory-drawing console process using trajectory logic and readings provided by an array of magnetic sensors on the ultrasound probe for determining the position and orientation of the needle.

Also disclosed herein is an ultrasound system with, in some embodiments, ultrasound-and-bioimpedance-based guidance for accessing a target within a patient. In such embodiments, the system includes an ultrasound probe, a medical device, a console, and a display screen. The ultrasound probe includes an array of ultrasound transducers. The array of ultrasound transducers is configured to emit ultrasound pulses into the patient and receive reflected ultrasound pulses reflected back through one or more tissues for producing ultrasound images. The medical device includes one or more needle electrodes in a distal portion of the medical device. The one-or-more needle electrodes are configured to emit, detect, or alternately emit and detect electrical currents passed through the one-or-more tissues disposed between a pair or more of system electrodes for measuring bioimpedance. The console includes one or more processors, primary memory including read-only memory ("ROM") and random-access memory ("RAM"), and instructions stored in the ROM. The instructions are configured to instantiate one or more console processes in the RAM for the ultrasound-and-bioimpedance-based guidance with the ultrasound probe and the medical device when operably connected to the console. The display screen is operably connected to the console for the ultrasound-and-bioimpedance-based guidance. The display screen is configured to display a graphical representation of the distal portion of the medical device among anatomical features of the patient in the ultrasound images confirmed by the bioimpedance of the one-or-more tissues previously or instantly disposed between the pair-or-more of system electrodes.

In some embodiments, the medical device is a needle, a guidewire, a catheter, a dilator, or an introducer sheath.

These and other features of the concepts provided herein will become more apparent to those of skill in the art in view of the accompanying drawings and following description, which describe particular embodiments of such concepts in greater detail.

DRAWINGS

DESCRIPTION

Figure 1:
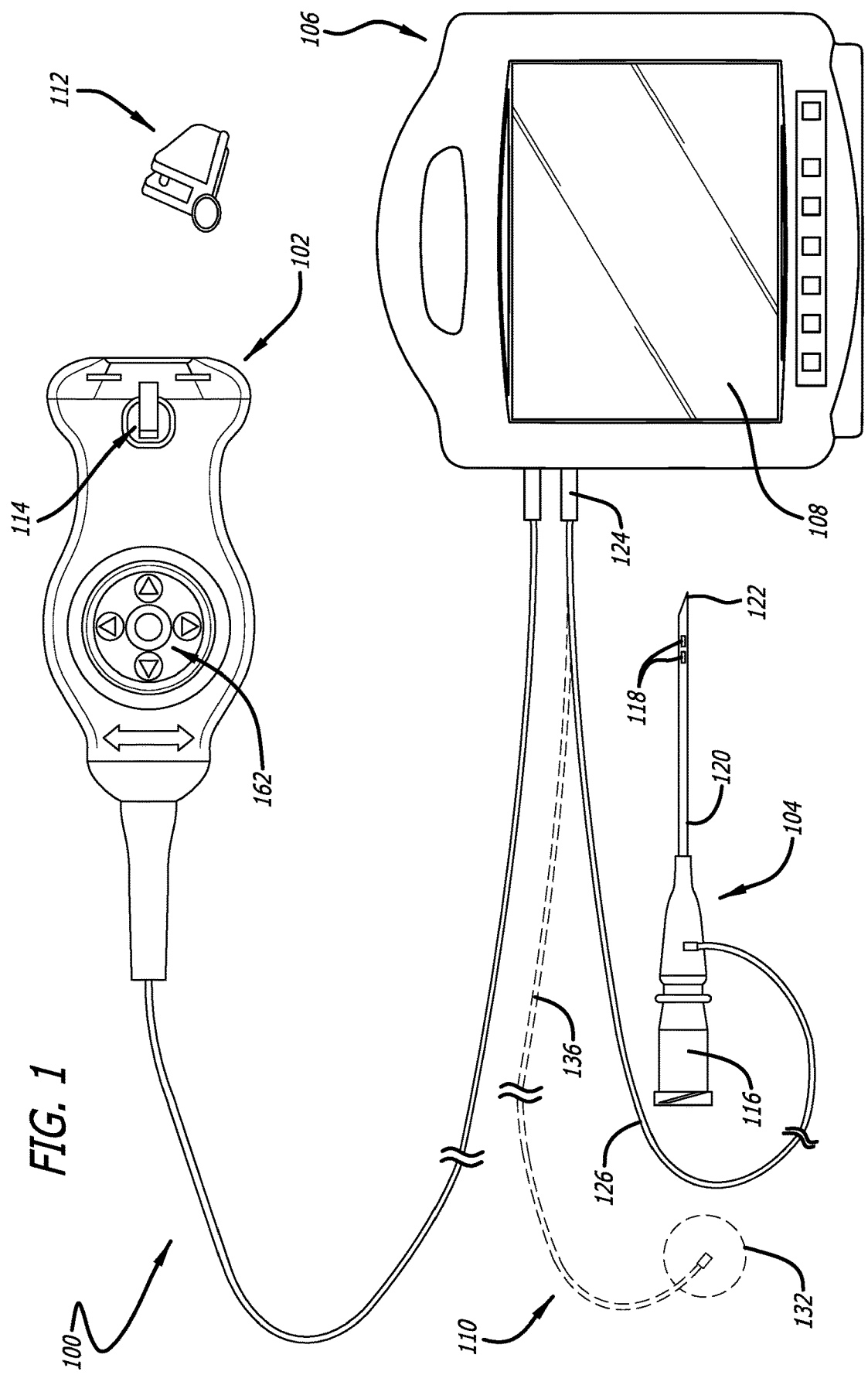
FIG. 1 illustrates a first ultrasound system with ultrasound-and-bioimpedance-based guidance in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, ultrasound-based guidance of medical devices is routine in a variety of medical procedures for diagnosing and treating diseases. Notwithstanding clear successes in the ultrasound-based guidance of medical devices for diagnosing and treating diseases, however, challenges to better diagnoses and treatments remain such as being able to differentiate between different tissues in ultrasound imagery. Disclosed herein are systems and methods for ultrasound-and-bioimpedance-based guidance of medical devices that address the foregoing.

Systems

Figure 2:
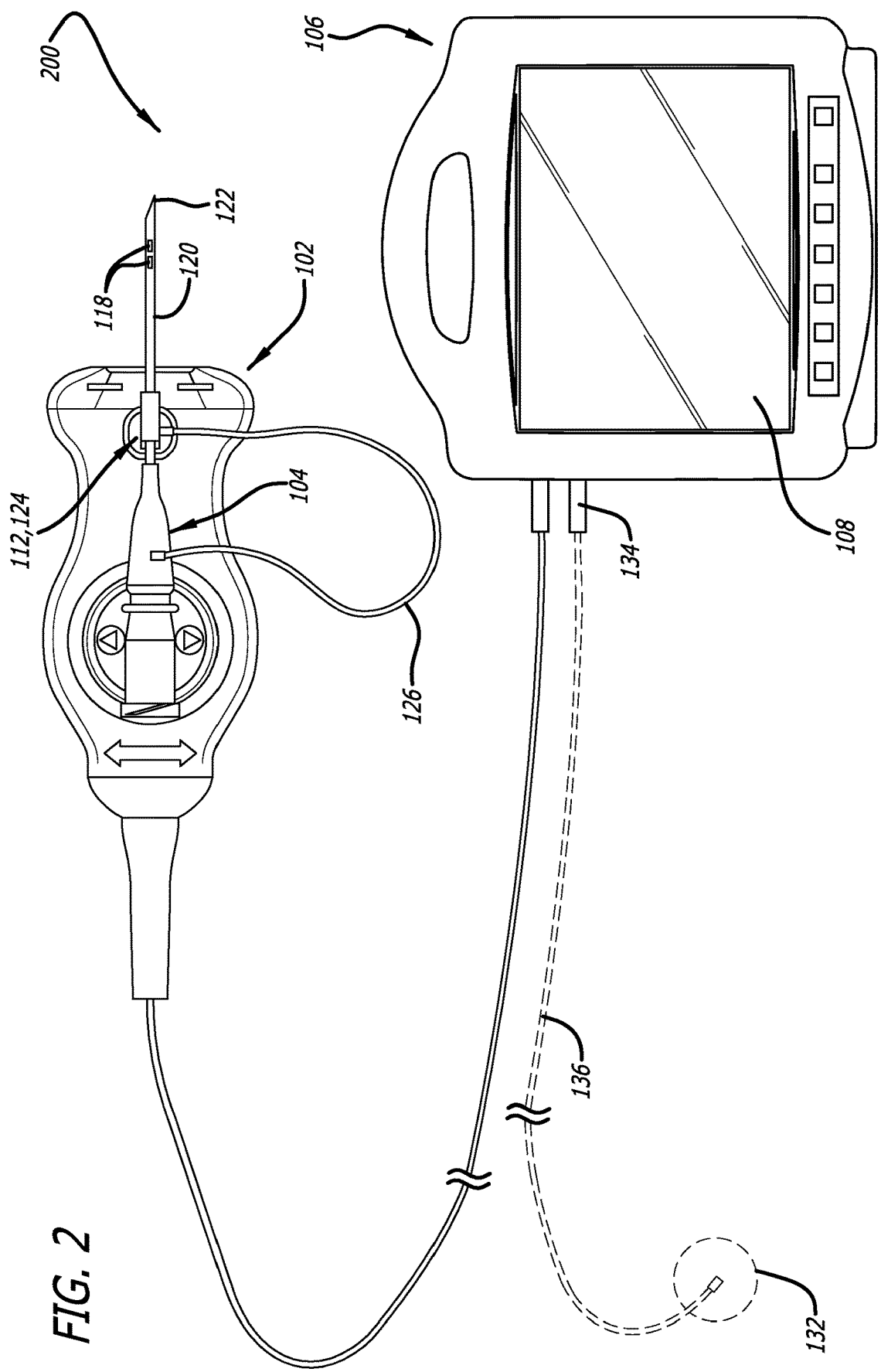
FIG. 2 illustrates a second ultrasound system with ultrasound-and-bioimpedance-based guidance in accordance with some embodiments.
Figure 4:
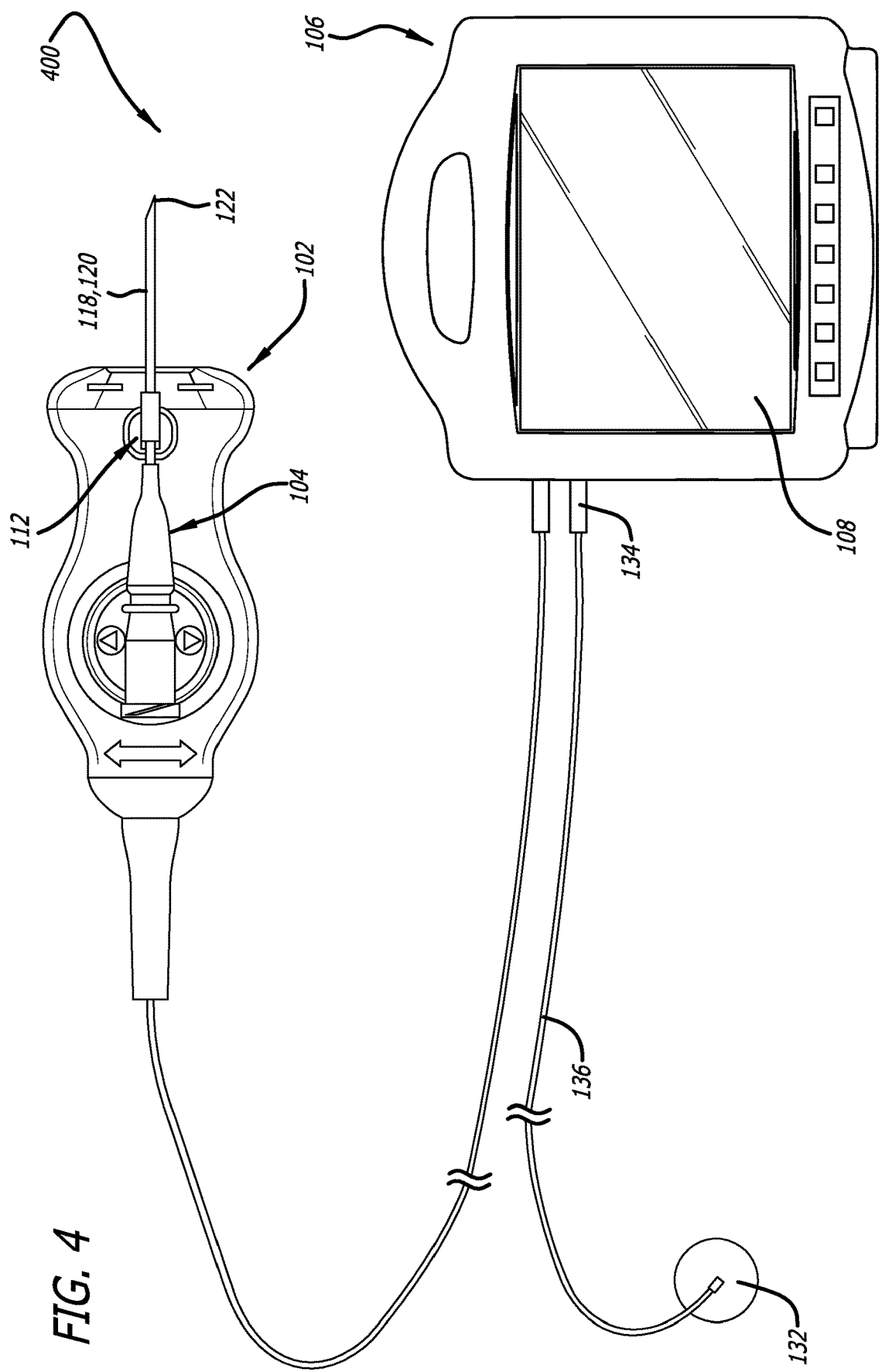
FIG. 4 illustrates a third system with ultrasound-and-bioimpedance-based guidance in accordance with some embodiments.

FIGS. 1, 2, and 4 illustrate ultrasound systems 100, 200, and 400 with ultrasound-and-bioimpedance-based guidance for accessing a target within a patient in accordance with some embodiments. Accessing the target of the patient can include gaining access to a vasculature of the patient for an intravascular procedure, access to a tumor of the patient for biopsy, access to a fluid-filled space of the patient for drainage. In addition, the system 100, 200, or 400 can be adapted such that after gaining access to the target of the patient, for example, in the vasculature of the patient, a needle such as the needle 104 can be exchanged for another medical device having one or more electrodes in a distal portion thereof such as a guidewire, a catheter, a dilator, an introducer sheath, etc. that can be similarly guided through the vasculature of the patient by way of ultrasound and bioimpedance as measured from one-or-more electrodes of the medical device.

As shown, the system 100, 200, or 400 includes an ultrasound probe 102, a needle 104, a console 106, and a display screen 108. The system can further include an electrode assembly 110, a needle guide 112, or both the electrode assembly 110 and the needle guide 112. Notably, the needle guide 112 and the ultrasound probe 102 can include electronic circuitry configured to operably connect the needle 104 to the console 102 when at least the needle guide 112 is coupled with a needle-guide attachment point 114 of the ultrasound probe 102. Description for each component of the ultrasound probe 102, the needle 104, the console 106, and the display screen 108 is set forth below beginning with the needle 104, the electrode assembly 110, the needle guide 112, and some corresponding features of the ultrasound probe 102, particularly those with respect to the electronic circuitry configured to operably connect the needle 104 to the console 102 when the needle guide 112 is coupled with the needle-guide attachment point 114 of the ultrasound probe 102.

The needle 104 includes a needle hub 116 and one or more needle electrodes 118 in a distal portion of a needle shaft 120 proximate a needle tip 122.

Figure 3:
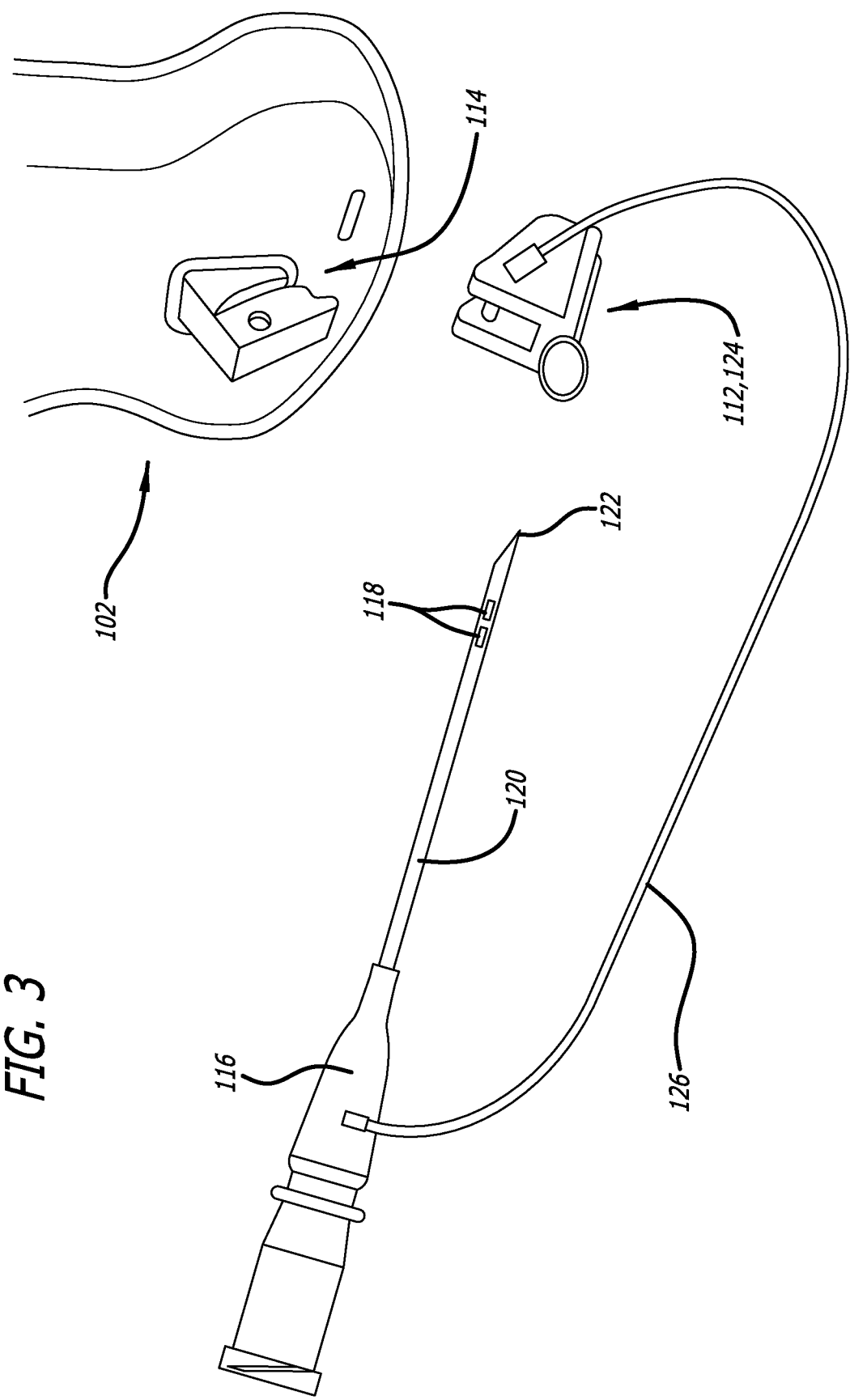
FIG. 3 illustrates a first needle with a first needle guide configured to operably connect the first needle to an ultrasound probe in accordance with some embodiments.

The one-or-more needle electrodes 118 are configured to emit, detect, or alternately emit and detect electrical currents passed through one-or-more tissues disposed between a pair or more of system electrodes for measuring bioimpedance. It should be understood that while the needle 104 of FIGS. 1-5 is shown with a particular number of needle electrodes 118, the number of needle electrodes 118 can vary. For example, the needle 104 of FIG. 1 is shown with two needle electrodes 118; however, the needle 104 of FIG. 1 can include a single needle electrode 118 when combined with the external electrode 132 of the electrode assembly 110. Alternatively, the needle 104 of FIG. 1 can include four needle electrodes 118. Likewise, the needle 104 of FIGS. 2 and 3 is shown with two needle electrodes 118; however, the needle 104 of FIGS. 2 and 3 can include a single needle electrode 118 when combined with the external electrode 132 of the electrode assembly 110. Alternatively, the needle 104 of FIGS. 2 and 3 can include four needle electrodes 118.

As to the pair-or-more of system electrodes, the pair-or-more of system electrodes can include one, two, three, four, or more needle electrodes 118. For example, the pair-or-more of system electrodes can include a combination of the one-or-more needle electrodes 118 and the external electrode 132 of the electrode assembly 110 such as a single needle electrode 118 in combination with the external electrode 132 of the electrode assembly 110 for monopolar bioimpedance measurements. Alternatively, the pair-or-more of system electrodes can include two or four needle electrodes 118 respectively for bipolar or tetrapolar bioimpedance measurements. However, it should be understood the pair-or-more of system electrodes are not limited to the foregoing examples. Indeed, another combination of the one-or-more needle electrodes 118 and the external electrode 132 of the electrode assembly 110 can include three needle electrodes 118 in combination with the external electrode 132 of the electrode assembly 110.

Adverting to FIGS. 1-3 and the primary embodiments shown therein, the needle 104 includes a pair of needle electrodes 118 as the pair-or-more of system electrodes for measuring bioimpedance; however, the needle 104 could alternatively include two pairs of needle electrodes 118 as the pair-or-more of system electrodes for measuring bioimpedance. In addition, the needle 104 further includes a needle connector 124 and a needle cable 126 between the needle hub 116 and the needle connector 124. The needle connector 124 and the needle cable 126 are configured to operably connect the needle 104 to the console 106 either directly or indirectly through the ultrasound probe 102. Indeed, as shown in FIGS. 2 and 3, the needle connector 124 is configured as the needle guide 112 (or the needle guide 112 is configured as the needle connector 124) for coupling with the needle-guide attachment point 114 of the ultrasound probe 102. In such embodiments, the needle connector 124 (or the needle guide 112), the needle cable 126 between the needle hub 116 and the needle connector 124 (or the needle guide 112), the needle-guide attachment point 114, and the ultrasound probe 102 include electronic circuitry therebetween configured to operably connect the needle 104 to the console 106 when the needle connector 124 (or the needle guide 112) is coupled with the needle-guide attachment point 114.

Figure 5:
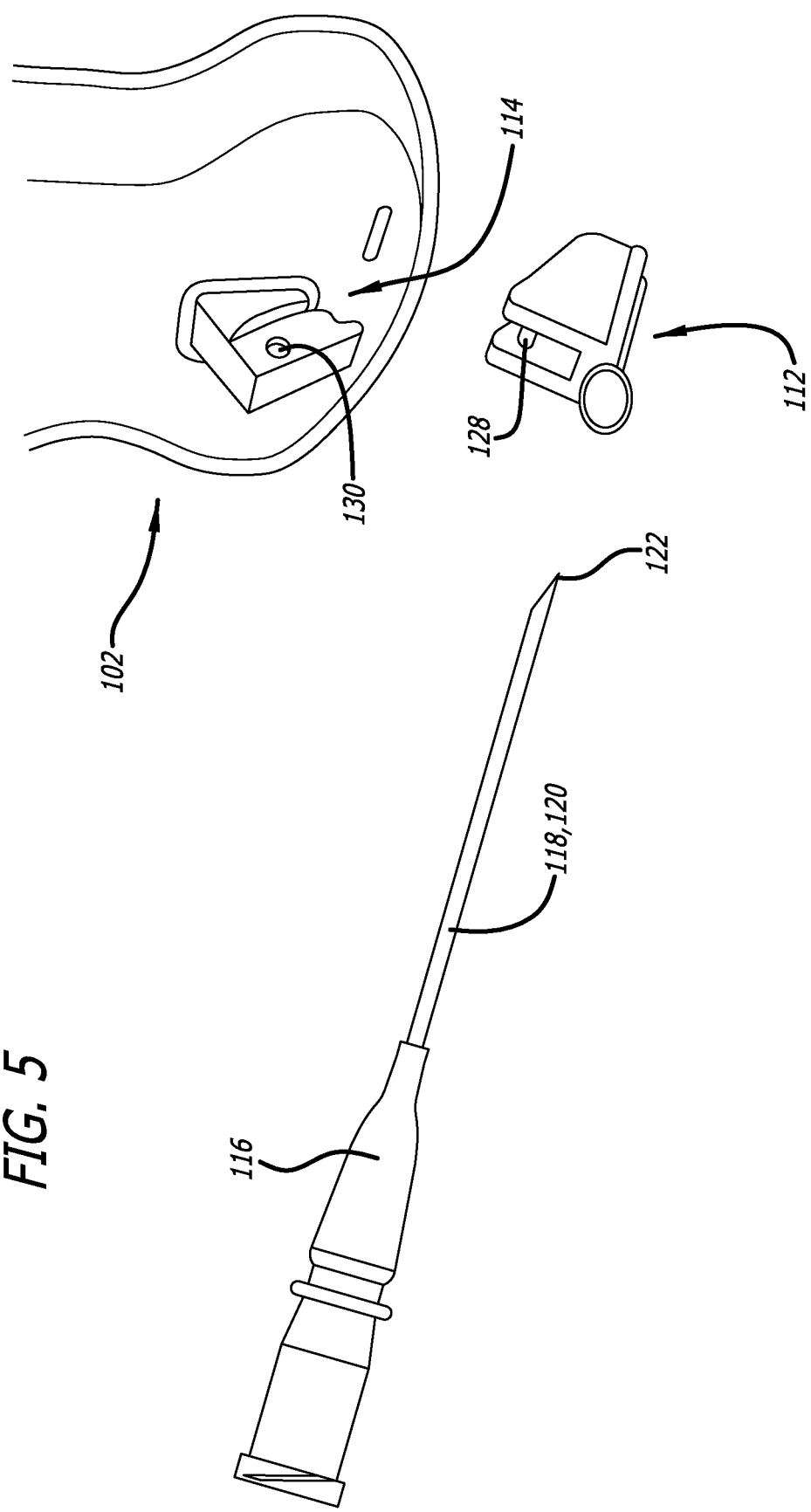
FIG. 5 illustrates a second needle with a second needle guide configured to operably connect the second needle to the ultrasound probe in accordance with some embodiments.

Adverting to FIGS. 4 and 5 and the primary embodiment shown therein, the needle 104 includes a single needle electrode 118 (e.g., the shaft 120) in combination with the external electrode 132 of the electrode assembly 110 as the pair-or-more of system electrodes for measuring bioimpedance. In addition, the system 400 further includes the needle guide 112 configured for coupling with the needle-guide attachment point 114 of the ultrasound probe 102. The needle guide 112, the needle-guide attachment point 114, and the ultrasound probe 102 include electronic circuitry configured to operably connect the needle 104 to the console 102 when the needle guide 112 is coupled with the needle-guide attachment point 114, the needle 104 is disposed in the needle guide 112, and the ultrasound probe 102 is connected to the console 106. Indeed, when the needle 104 is inserted into the needle guide 112, the shaft 120 makes electrical contact with a ring electrical contact within the needle guide 112 to operably connect the needle 104 to the console 102 when the needle guide 112 is coupled with the needle-guide attachment point 114, the needle 104 is disposed in the needle guide 112, and the ultrasound probe 102 is connected to the console 106.

The needle guide 112 and the needle-guide attachment point 114 can be mechanically and electrically coupled by way of complementary connecting features. Indeed, the needle guide 112 can include conductive inward-facing protrusions 128 and the needle-guide attachment point 114 can include outward-facing receptacles 130. The protrusions 128 of the needle guide 112 are configured to establish an electrical connection with the receptacles 130 of the needle-guide attachment point 114 when the needle guide 112 is coupled with the needle-guide attachment point 114. In some embodiments, the protrusions 128 can include barrier-piercing points. Such barrier-piercing points of the protrusions 128 are configured to pierce a film-based single patient-use protective barrier when used over the ultrasound probe 102 and, thereby, establish the electrical connection with the receptacles 130 of the needle-guide attachment point 114. Being complementary, the receptacles 130 are shaped to accommodate the barrier-piercing points of the protrusions 128.

As to the electrode assembly 110, the electrode assembly 110 includes an external electrode 132, an electrode-assembly connector 134, and an electrode-assembly cable 136 between the external electrode 132 and the electrode-assembly electrode connector 134. The external electrode 132 is configured to be adhered to skin of the patient for measuring bioimpedance. The electrode-assembly connector 134 is configured to be connected to the console 106. The electrode-assembly cable 136 is configured to operably connect the external electrode 132 to the console 106 through the electrode-assembly connector 134.

Figure 6:
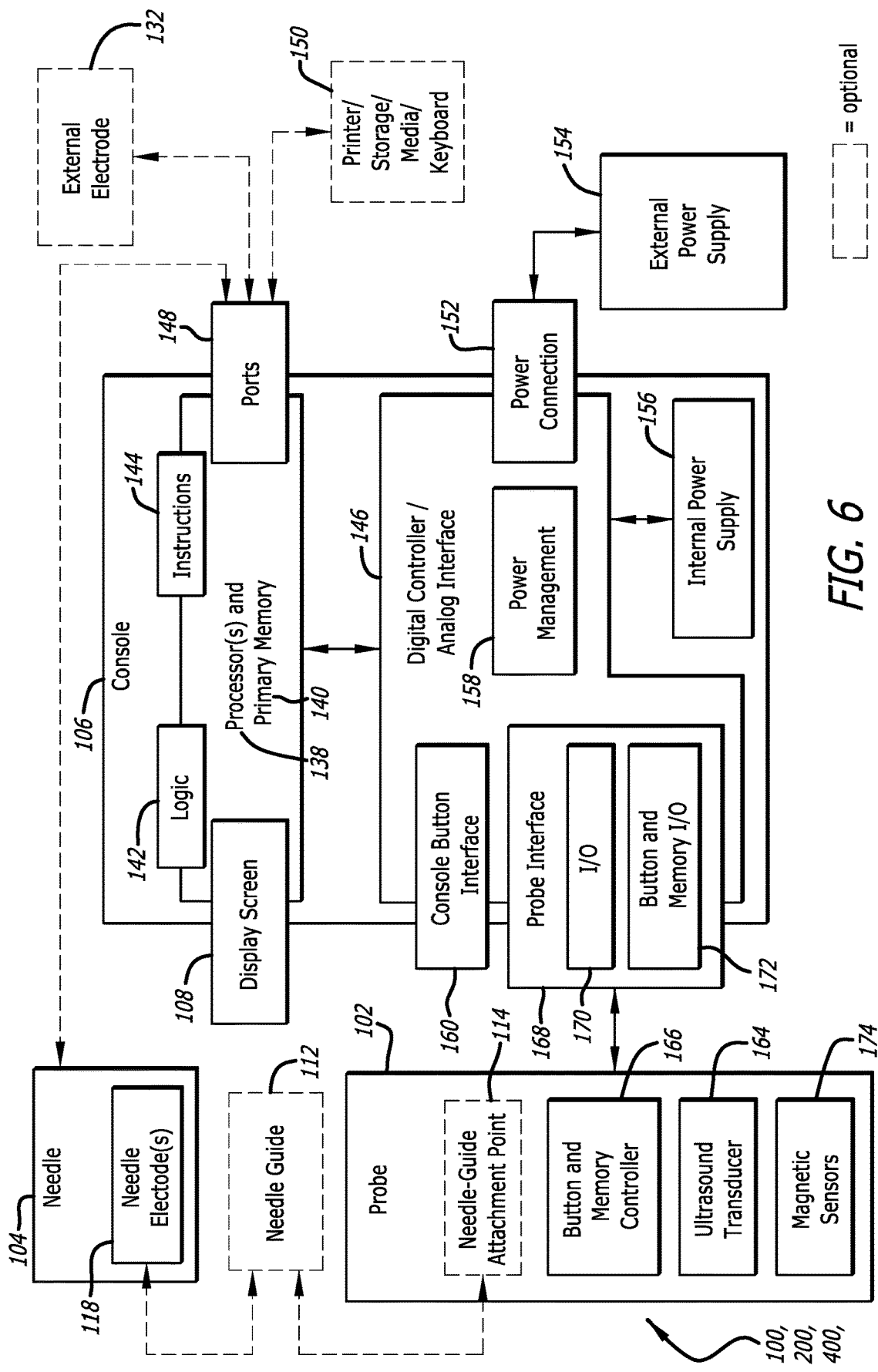
FIG. 6 illustrates block diagram of the ultrasound system of FIG. 1, 2, or 4 in accordance with some embodiments.

FIG. 6 illustrates block diagram of the ultrasound system 100, 200, or 400 in accordance with some embodiments.

The console 106 houses and accommodates a variety of components of the system 100, 200, or 400, and it is appreciated the console 106 can take any form of a variety of forms. One or more processors 138 and primary memory 140 such as ROM (e.g., electrically erasable programmable read-only memory ["EEPROM"]) and RAM is included in the console 106 for controlling various functions of the system 100, 200, or 400, as well as executing various logic operations of logic 142 during operation of the system 100, 200, or 400. As for operating the system 100, 200, or 400, the console 106 is configured to instantiate by way of executable instructions 144 stored in the ROM one or more console processes in the RAM for the ultrasound-and-bioimpedance-based guidance with the ultrasound probe 102 and the needle 104 when operably connected to the console 106. A digital controller/analog interface 146 is also included with the console 106 and is in communication with both the one-or-more processors 138 and other system components to govern interfacing between the ultrasound probe 102 and other system components set forth herein.

The console 106 further includes ports 148 for connection with additional components such as the needle 104, the external electrode 132, and optional components 150 including a printer, storage media, keyboard, etc. The ports 148 can be universal serial bus ("USB") ports, though other types of ports can be used for this connection or any other connections shown or described herein. A power connection 152 is included with the console 106 to enable operable connection to an external power supply 154. An internal power supply 156 (e.g., a battery) can also be employed either with or exclusive of the external power supply 154. Power management circuitry 158 is included with the digital controller/analog interface 146 of the console 106 to regulate power use and distribution.

Figure 9:
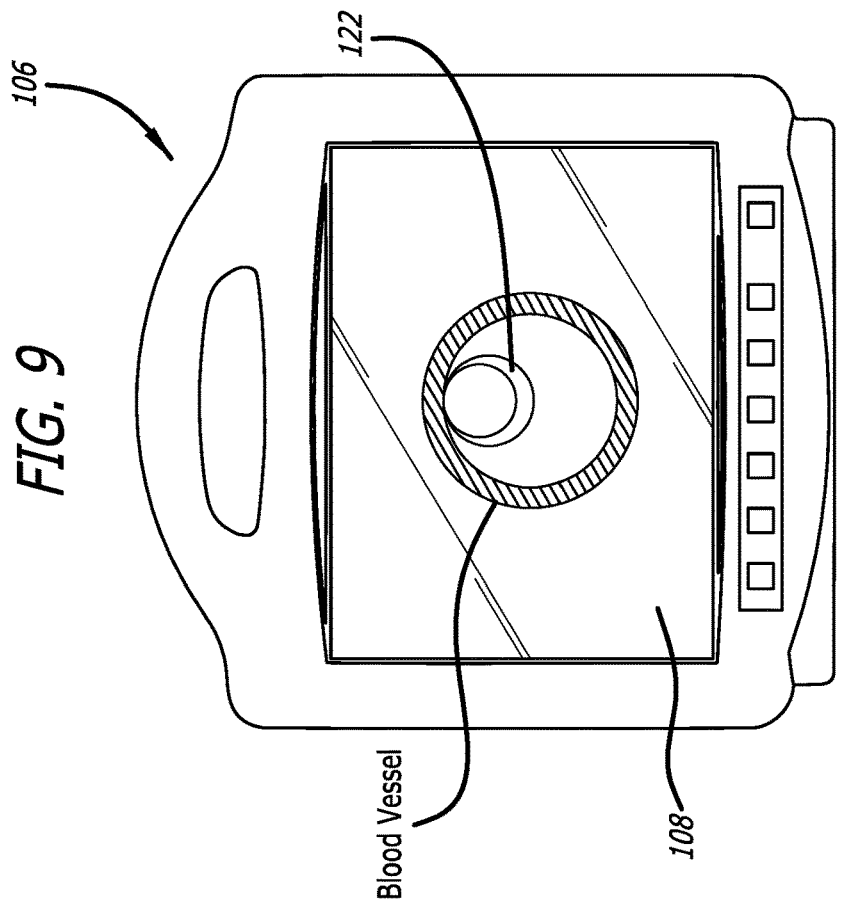
FIG. 9 illustrates an ultrasound image of the first needle transitioning from subcutaneous tissue to that of a blood vessel on a console of the ultrasound system in accordance with some embodiments.

The display screen 108 (e.g., a liquid-crystal display ["LCD"] screen) is operably connected to the console 106 for the ultrasound-and-bioimpedance-based guidance. As shown, the display screen 108 can be integrated into the console 160 to provide a graphical user interface ("GUI") and display information for a clinician during such as ultrasound images of attained by the ultrasound probe 102. Alternatively, the display screen 108 is separate from the console 106 and communicatively coupled thereto. Regardless, the display screen 108 is configured to display a graphical representation of the needle 104 or the distal portion of the other medical device (e.g., the guidewire, the catheter, the dilator, the introducer sheath, etc.) among anatomical features of the patient in the ultrasound images (see FIG. 9) confirmed by the bioimpedance of one-or-more tissues previously or instantly disposed between the pair-or-more of system electrodes. Indeed, FIG. 9 illustrates an ultrasound image of the needle 104 transitioning from subcutaneous tissue to that of a blood vessel on the console 106 of the ultrasound system 100, 200, or 400 in accordance with FIG. 8. A console button interface 160 and control buttons 162 included on the ultrasound probe 102 can be used to immediately call up a desired mode to the display screen 108 by the clinician for the ultrasound-and-bioimpedance-based guidance.

The ultrasound probe 102 includes a probe head that houses an array of ultrasound transducers 164, wherein the ultrasound transducers 164 are piezoelectric transducers or capacitive micromachined ultrasound transducers ("CMUTs") configured to emit ultrasound pulses into a patient and receive reflected ultrasound pulses reflected back through one or more tissues for producing ultrasound images. The probe head is configured for placement against skin of the patient over the needle 104. In this way, the system 100, 200, or 400, by way of the ultrasound probe 104 and the logic 142, can provide the ultrasound-and-bioimpedance-based guidance.

The ultrasound probe 102 also includes a button-and-memory controller 166 for governing button operation, as well as governing operation of the ultrasound probe 102. The button-and-memory controller 166 can include ROM (e.g., EEPROM). The button-and-memory controller 166 is in operable communication with a probe interface 168 of the console 106, which includes an input/output ("I/O") component 170 for interfacing with the ultrasound transducers 164 and a button-and-memory I/O component 172 for interfacing with the button-and-memory controller 166.

As set forth above, the instructions 144 are configured to instantiate one or more console processes in the RAM for the ultrasound-and-bioimpedance-based guidance with the ultrasound probe 102 and the needle 104 when operably connected to the console 106. The one-or-more console processes can include an ultrasound image-producing console process, a bioimpedance-measuring console process, and a correlating console process. The ultrasound image-producing console process is configured for producing the ultrasound images of anatomical features from reflected ultrasound pulses. The bioimpedance-measuring console process is configured for measuring bioimpedance from electrical currents passed through one or more tissues disposed between the pair-or-more of system electrodes. The correlating console process is configured for correlating the bioimpedance of the one-or-more tissues with the anatomical features in the ultrasound images. The correlating console process is in accordance with correlating logic and at least the bioimpedance of the one-or-more tissues.

The one-or-more console processes can also include a colorizing console process. The colorizing console process is configured for colorizing the one-or-more tissues of the ultrasound images on the display screen 108. The colorizing console process is in accordance with colorizing logic and at least the bioimpedance of the one-or-more tissues.

Figure 8:
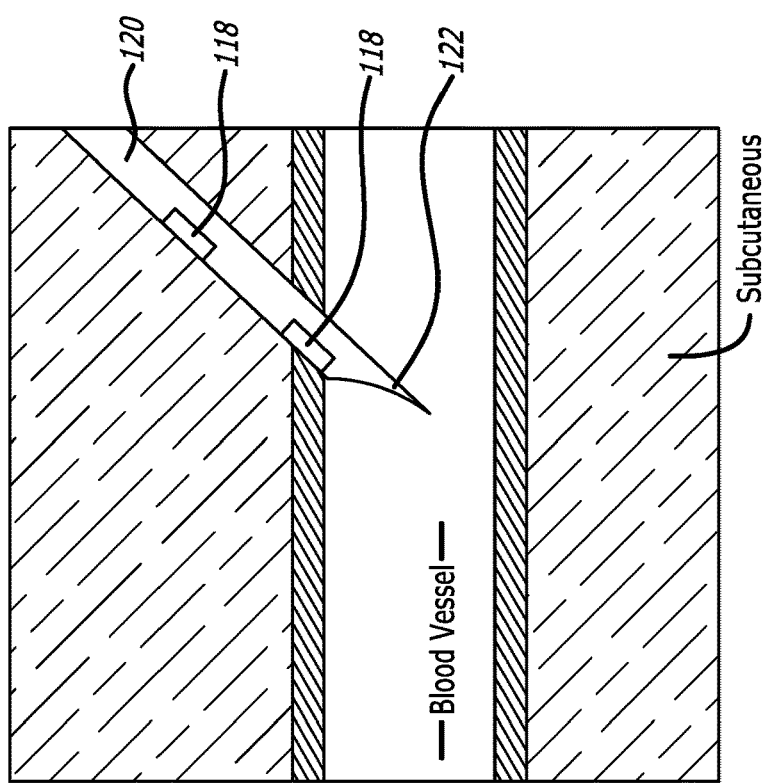
FIG. 8 illustrates the first needle transitioning from subcutaneous tissue to that of a blood vessel in accordance with some embodiments.
Figure 10:
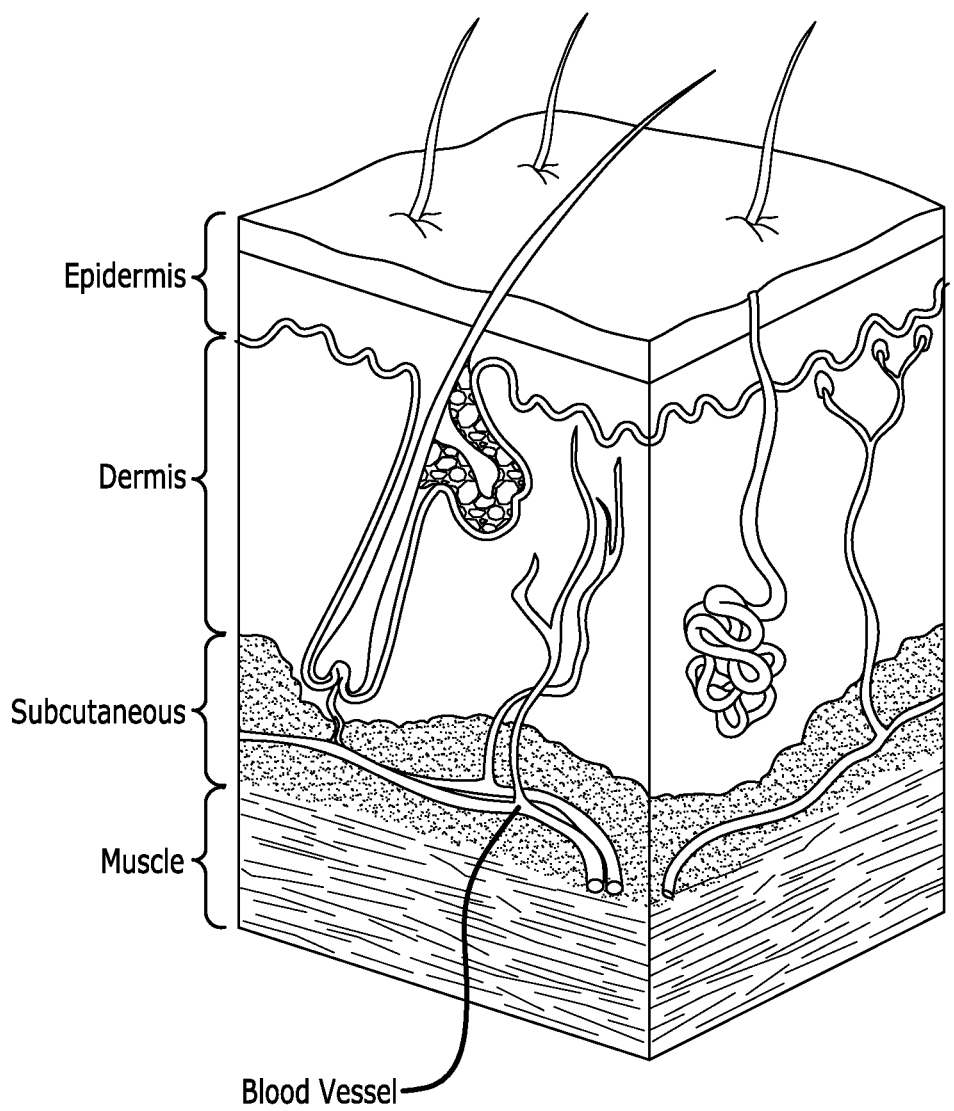
FIG. 10 illustrates a variety of different tissues in accordance with some embodiments.

The one-or-more console processes can also include a tissue transition-alerting console process. The tissue transition-alerting console process is configured for issuing a tissue-transition alert by way of an on-screen graphical alert, a system speaker-emitted alert, a needle-generated tactile alert, or the like when the needle 104 transitions from a tissue to another tissue of the one-or-more tissues such as subcutaneous tissue and blood-vessel tissue (e.g., tunica adventitia, tunica media, or tunica intima) as shown in FIG. 8. Indeed, transitions from a tissue to another tissue of the one-or-more tissues can include, but are not limited to, a transitions between cutaneous tissue (e.g., dermal tissue) and subcutaneous tissue; subcutaneous tissue and nerve tissue; subcutaneous tissue and muscle; muscle and nerve tissue; cutaneous tissue (e.g., dermal tissue) and blood-vessel tissue (e.g., tunica adventitia, tunica media, or tunica intima); subcutaneous tissue and blood-vessel tissue (e.g., tunica adventitia, tunica media, or tunica intima); muscle and blood-vessel tissue (e.g., tunica adventitia, tunica media, or tunica intima); nerve tissue and blood-vessel tissue (e.g., tunica adventitia, tunica media, or tunica intima); muscle or tissue of the parietal pleura and pleural fluid of the pleural cavity; tissue of the meninges (e.g., dura mater membrane or arachnoid mater membrane) and cerebrospinal fluid; any tissue and a fluid for drainage; or healthy tissue and a tumor. (See, for example, FIG. 10 for some of the foregoing tissues.) The tissue transition-alerting console process is in accordance with tissue-transition logic and at least the bioimpedance of the one-or-more tissues.

Figure 7:
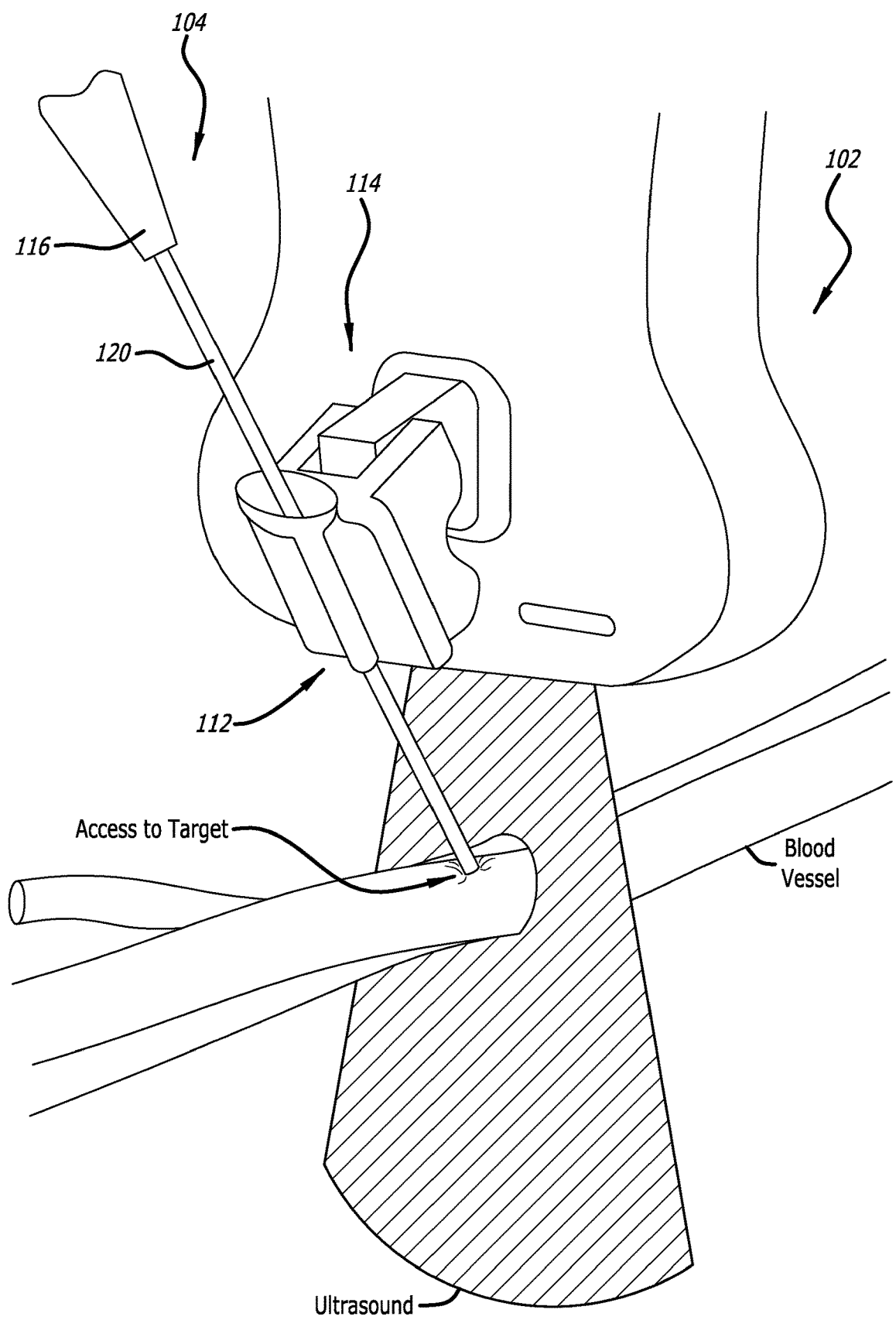
FIG. 7 illustrates the first or second needle accessing a blood vessel while respectively loaded in the first or second needle guide in accordance with some embodiments.

The one-or-more console processes can also include an access-confirming console process. The access-confirming console process is configured for confirming access to a target such as a blood vessel as shown in FIG. 7 by way of an on-screen graphical confirmation, a system speaker-emitted audible confirmation, a needle-generated tactile confirmation, or the like. The access-confirming console process is in accordance with access-confirmation logic and at least the bioimpedance of the one-or-more tissues.

The one-or-more console processes can also include a warning-issuing console process. The warning-issuing console process is configured for issuing a warning by way of an on-screen graphical warning, a system speaker-emitted audible warning, a needle-generated tactile warning, or the like when access to a target is at risk of being lost (e.g., back-walling a blood vessel). The warning-issuing console process is in accordance with warning logic and at least the bioimpedance of the one-or-more tissues.

The one-or-more console processes can also include a trajectory-drawing console process. The trajectory-drawing console process is configured for drawing a trajectory (e.g., a line or arrow) on the display screen 108 from the graphical representation of the needle 104 to a target. The trajectory-drawing console process is in accordance with trajectory logic and readings provided by an array of magnetic sensors 174 on the ultrasound probe 102 for determining the position and orientation of the needle 104.

Methods

Methods for ultrasound-and-bioimpedance-based guidance of medical devices include a method of the system 100, 200, or 400 for accessing a target within a patient. Such a method includes an instantiating step, a plurality of ultrasound image-producing steps, a bioimpedance-measuring step, and a displaying step.

The instantiating step includes instantiating the one-or-more console processes in the RAM of the console 106 from the instructions 144 stored in the ROM of the console 106. The one-or-more processors 138 of the console 106 are configured to process at least reflected ultrasound pulses and detected electrical currents for the ultrasound-and-bio-impedance-based guidance.

The plurality of ultrasound image-producing steps include producing ultrasound images of anatomical features of the patient in accordance with the ultrasound image-producing console process. The ultrasound image-producing console process is configured for processing the reflected ultrasound pulses resulting from ultrasound pulses emitted into the patient by the ultrasound probe 102 and subsequently reflected back through one or more tissues of the patient.

The bioimpedance-measuring step includes measuring bioimpedance of the one-or-more tissues in accordance with the bioimpedance-measuring console process. The bioimpedance-measuring console process is configured for processing the detected electrical currents passed through the one-or-more tissues when disposed between the pair-or-more of system electrodes including the one-or-more needle electrodes 118 of the needle 104.

The displaying step includes displaying on the display screen 108 a graphical representation of the needle 104 among the anatomical features in the ultrasound images. The anatomical features are confirmed by the bioimpedance of the one-or-more tissues previously or instantly disposed between the pair-or-more of system electrodes.

The method can further include a correlating step. The correlating step includes correlating the bioimpedance of the one-or-more tissues with the anatomical features in the ultrasound images. The correlating step is performed in accordance with the correlating console process using the correlating logic and at least the bioimpedance of the one-or-more tissues.

The method can further include a colorizing step. The colorizing step includes colorizing the one-or-more tissues of the ultrasound images on the display screen 108. The colorizing step is performed in accordance with the colorizing console process using the colorizing logic and at least the bioimpedance of the one-or-more tissues.

The method can further include an alert-issuing step. The alert-issuing step includes issuing a tissue-transition alert by way of an on-screen graphical alert, a system speaker-emitted alert, a needle-generated tactile alert, or the like when the needle 104 transitions from a tissue to another tissue of the one-or-more tissues such as subcutaneous tissue and blood-vessel tissue (e.g., tunica adventitia, tunica media, or tunica intima) as shown in FIG. 8. The tissue-transition alert is performed in accordance with the tissue transition-alerting console process using the tissue-transition logic and at least the bioimpedance of the one-or-more tissues.

The method can further includes an access-confirming step. The access-confirming step includes confirming access to the target such as a blood vessel as shown in FIG. 7 by way of an on-screen graphical confirmation, a system speaker-emitted audible confirmation, a needle-generated tactile confirmation, or the like. The access-confirming step is performed in accordance with the access-confirming console process using the access-confirmation logic and at least the bioimpedance of the one-or-more tissues.

The method further includes a warning-issuing step. The warning-issuing step includes issuing a warning by way of an on-screen graphical warning, a system speaker-emitted audible warning, a needle-generated tactile warning, or the like when access to the target is at risk of being lost (e.g., back-walling a blood vessel). The warning-issuing step is performed in accordance with the warning-issuing console process using the warning logic and at least the bioimpedance of the one-or-more tissues.

The method further includes a trajectory-drawing step. The trajectory-drawing step includes drawing a trajectory (e.g., a line or arrow) on the display screen 108 from the graphical representation of the needle 104 to the target. The trajectory-drawing step is performed in accordance with the trajectory-drawing console process using the trajectory logic and readings provided by the array of magnetic sensors 174 on the ultrasound probe 102 for determining the position and orientation of the needle 104.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound system with ultrasound-and-bioimpedance-based guidance configured for accessing a target within a patient, comprising:
   one or more pairs of system electrodes;
   an ultrasound probe including:
      an array of ultrasound transducers configured to emit ultrasound pulses into the patient and receive reflected ultrasound pulses reflected back through one or more tissues for producing ultrasound images; and
      a needle-guide attachment point;
   a needle including a needle hub and one or more needle electrodes in a distal portion of a needle shaft proximate a needle tip, the one or more needle electrodes configured to emit, detect, or alternately emit and detect electrical currents passed through the one or more tissues disposed between the one or more pairs of system electrodes for measuring bioimpedance,
      wherein the one or more pairs of system electrodes comprises the one or more needle electrodes;
   a console including one or more processors, primary memory including read-only memory (ROM) and random-access memory (RAM), and instructions stored in the ROM configured to instantiate one or more console processes in the RAM for the ultrasound-and-bioimpedance-based guidance with the ultrasound probe and the needle when operably connected to the console;
   a needle guide configured to operably connect the needle to the console, the needle guide including:
      a ring electrical contact configured to establish an electrical connection with the needle when the needle is inserted into the needle guide; and
      conductive inward-facing protrusions configured to establish an electrical connection with outward-facing receptacles of the needle-guide attachment point when the needle guide is coupled with the needle-guide attachment point of the ultrasound probe; and
   a display screen operably connected to the console for the ultrasound-and-bioimpedance-based guidance, the display screen configured to display a graphical representation of the needle among anatomical features of the patient in the ultrasound images,
      wherein the anatomical features are confirmed by the bioimpedance of the one or more tissues previously or instantly disposed between the one or more pairs of system electrodes.

2. The ultrasound system of claim 1, wherein the one or more needle electrodes include a single needle electrode.

3. The ultrasound system of claim 2, wherein the conductive inward-facing protrusions include barrier-piercing points configured to a) pierce a protective film-based barrier when used over the ultrasound probe and b) establish the electrical connection with the outward-facing receptacles of the needle-guide attachment point, the outward-facing receptacles being shaped to accommodate the barrier-piercing points of the conductive inward-facing protrusions.

4. The ultrasound system of claim 2, the needle further comprising a needle connector and a needle cable, the needle connector configured to operably connect the needle hub of the needle to the console via the needle cable.

5. The ultrasound system of claim 2, further comprising an electrode assembly including an external electrode configured to be adhered to skin of the patient, an electrode-assembly connector configured to be connected to the console, and an electrode-assembly cable between the external electrode and the electrode-assembly connector configured to operably connect the external electrode to the console though the electrode-assembly connector, the single needle electrode and the external electrode being the one or more pairs of system electrodes for measuring bioimpedance.

6. The ultrasound system of claim 1, wherein the one or more needle electrodes include a pair of needle electrodes, the pair of needle electrodes being the one or more pairs of system electrodes for measuring bioimpedance.

7. The ultrasound system of claim 6, the needle further comprising a needle cable between the needle hub and the needle guide configured to operably connect the needle to the console when a needle connector is coupled with the needle-guide attachment point.

8. The ultrasound system of claim 6, the needle further comprising a needle connector and a needle cable, the needle connector configured to operably connect the needle hub of the needle to the console via the needle cable.

9. The ultrasound system of claim 1, wherein the one or more needle electrodes include two pairs of needle electrodes, the two pairs of needle electrodes being the one or more pairs of system electrodes for measuring bioimpedance.

10. The ultrasound system of claim 1, the one or more console processes including:
   an ultrasound image-producing console process for producing the ultrasound images of the anatomical features from the reflected ultrasound pulses;
   a bioimpedance-measuring console process for measuring the bioimpedance from the electrical currents passed through the one or more tissues disposed between the one or more pairs of system electrodes; and
   a correlating console process for correlating the bioimpedance of the one or more tissues with the anatomical features in the ultrasound images, the correlating console process in accordance with correlating logic and at least the bioimpedance of the one or more tissues.

11. The ultrasound system of claim 10, the one or more console processes further including a colorizing console process for colorizing the one or more tissues of the ultrasound images on the display screen, the colorizing console process in accordance with colorizing logic and at least the bioimpedance of the one or more tissues.

12. The ultrasound system of claim 10, the one or more one or more console processes further including a tissue transition-alerting console process for issuing a tissue-transition alert when the needle transitions from a first tissue to a second tissue of the one or more tissues, the tissue transition-alerting console process in accordance with tissue-transition logic and at least the bioimpedance of the one or more tissues.

13. The ultrasound system of claim 10, the one or more console processes further including an access-confirming console process for confirming access to the target, the access-confirming console process in accordance with access-confirmation logic and at least the bioimpedance of the one or more tissues.

14. The ultrasound system of claim 10, the one or more console processes further including a warning-issuing console process for issuing a warning when access to the target is at risk of being lost, the warning-issuing console process in accordance with warning logic and at least the bioimpedance of the one or more tissues.

15. The ultrasound system of claim 12, the one or more console processes further including a trajectory-drawing console process for drawing a trajectory on the display screen from the graphical representation of the needle to the target, the trajectory-drawing console process in accordance with trajectory logic and readings provided by an array of magnetic sensors on the ultrasound probe for determining a position and orientation of the needle.

16. A method of an ultrasound system configured for accessing a target within a patient with ultrasound-and-bioimpedance-based guidance, comprising:

instantiating one or more processes in random-access memory (RAM) of a console from instructions stored in read-only memory (ROM) of the console, one or more console processors of the console configured to process at least reflected ultrasound pulses and detected electrical currents for the ultrasound-and-bioimpedance-based guidance;

producing ultrasound images of anatomical features of the patient in accordance with an ultrasound image-producing console process for processing the at least reflected ultrasound pulses resulting from ultrasound pulses emitted into the patient by an ultrasound probe and subsequently reflected back through one or more tissues of the patient;

measuring bioimpedance of the one or more tissues in accordance with a bioimpedance-measuring console process for processing the detected electrical currents passed through the one or more tissues when disposed between one or more pairs of system electrodes comprises one or more needle electrodes of a needle, wherein the needle is operably connected to the console by a needle guide including:

a ring electrical contact establishing an electrical connection with the needle while the needle is inserted into the needle guide; and conductive inward-facing protrusions establishing an electrical connection with outward-facing receptacles of a needle-guide attachment point of the ultrasound probe while the needle guide is coupled with the needle-guide attachment point of the ultrasound probe; and displaying on a display screen a graphical representation of the needle among the anatomical features in the ultrasound images, wherein the anatomical features are confirmed by the bioimpedance of the one or more tissues previously or instantly disposed between the one or more pairs of system electrodes.

17. The method of claim 16, further comprising correlating the bioimpedance of the one or more tissues with the anatomical features in the ultrasound images in accordance with a correlating console process using correlating logic and at least the bioimpedance of the one or more tissues.

18. The method of claim 16, further comprising colorizing the one or more tissues of the ultrasound images on the display screen in accordance with a colorizing console process using colorizing logic and at least the bioimpedance of the one or more tissues.

19. The method of claim 16, further comprising issuing a tissue-transition alert when the needle transitions from a first tissue to a second tissue of the one or more tissues in accordance with a tissue transition-alerting console process using tissue-transition logic and at least the bioimpedance of the one or more tissues.

20. The method of claim 16, further comprising confirming access to the target in accordance with an access-confirming console process using access-confirmation logic and at least the bioimpedance of the one or more tissues.

21. The method of claim 16, further comprising issuing a warning when access to the target is at risk of being lost in accordance with a warning-issuing console process using warning logic and at least the bioimpedance of the one or more tissues.

22. The method of claim 16, further comprising drawing a trajectory on the display screen from the graphical representation of the needle to the target in accordance with a trajectory-drawing console process using trajectory logic and readings provided by an array of magnetic sensors on the ultrasound probe for determining a position and orientation of the needle.

* * * * *